United States Patent
Schmitt et al.

(10) Patent No.: US 11,150,652 B2
(45) Date of Patent: Oct. 19, 2021

(54) METHOD FOR OPERATING A DRIVER ASSISTANCE DEVICE OF A MOTOR VEHICLE

(71) Applicant: AUDI AG, Ingolstadt (DE)

(72) Inventors: Nicholas Schmitt, Ingolstadt (DE); Stefan Maiwald, Ingolstadt (DE)

(73) Assignee: Audi AG, Ingolstadt (DE)

( * ) Notice: Subject to any disclaimer, the term of this patent is extended or adjusted under 35 U.S.C. 154(b) by 246 days.

(21) Appl. No.: 16/469,558

(22) PCT Filed: Dec. 11, 2017

(86) PCT No.: PCT/EP2017/082218
§ 371 (c)(1),
(2) Date: Jun. 13, 2019

(87) PCT Pub. No.: WO2018/114431
PCT Pub. Date: Jun. 28, 2018

(65) Prior Publication Data
US 2020/0117190 A1   Apr. 16, 2020

(30) Foreign Application Priority Data
Dec. 20, 2016  (DE) .......................... 102016225606.8

(51) Int. Cl.
*G05D 1/00* (2006.01)
*A61B 5/00* (2006.01)
(Continued)

(52) U.S. Cl.
CPC ......... *G05D 1/0061* (2013.01); *A61B 5/0077* (2013.01); *A61B 5/18* (2013.01);
(Continued)

(58) Field of Classification Search
CPC .................................................. G05D 1/0061
See application file for complete search history.

(56) References Cited

U.S. PATENT DOCUMENTS

| 5,448,479 | A | 9/1995 | Kemner et al. |
| 6,516,255 | B2 * | 2/2003 | Jager ............. F16D 48/06 701/29.2 |

(Continued)

FOREIGN PATENT DOCUMENTS

| DE | 102009040221 A1 | 3/2011 |
| DE | 102009041587 A1 | 3/2011 |

(Continued)

OTHER PUBLICATIONS

International Search Report and Written Opinion of the International Searching Authority directed to related International Patent Application No. PCT/EP2017/082218, dated Feb. 1, 2018, with attached English-language translation; 17 pages.

(Continued)

*Primary Examiner* — Alex C Dunn
(74) *Attorney, Agent, or Firm* — Sterne, Kessler, Goldstein & Fox P.L.L.C.

(57) ABSTRACT

The invention relates to a method for operating a driver assistance system of a motor vehicle, wherein the motor vehicle is initially operated in a piloted or fully autonomous driving mode by a driver assistance device. Piloting data is provided by a control device of the motor vehicle, which describes at least one operating parameter of a motor vehicle system of the motor vehicle or the surroundings of the motor vehicle, and are navigation data. It is checked whether a totality of the provided piloting data meets a piloting condition, which stipulates a minimum requirement for the totality of the provided piloting data for implementing the piloted or fully autonomous driving mode. Upon failure to meet the piloting condition, an abort of the driving mode is determined and a driving situation signal is generated, which describes the piloting data and this signal is transmitted to a communication unit of a motor vehicle-external server device. The control device receives at least one control (Continued)

signal from the motor vehicle-external server device and transmits this control signal to the driver assistance device.

15 Claims, 1 Drawing Sheet

(51) Int. Cl.
    *A61B 5/18*           (2006.01)
    *B60W 50/00*       (2006.01)
    *G05D 1/02*         (2020.01)

(52) U.S. Cl.
    CPC .......... *A61B 5/4809* (2013.01); *A61B 5/6893* (2013.01); *B60W 50/0098* (2013.01); *G05D 1/0276* (2013.01); *B60W 2540/22* (2013.01); *G05D 2201/0213* (2013.01)

(56) References Cited

U.S. PATENT DOCUMENTS

| | | | |
|---|---|---|---|
| 8,433,503 B2 * | 4/2013 | Miyakoshi | G08G 1/164 701/117 |
| 9,494,935 B2 | 11/2016 | Okumura et al. | |
| 10,295,054 B2 * | 5/2019 | Armstead | F16H 61/0213 |
| 2002/0111732 A1 * | 8/2002 | Jager | F16D 48/06 701/62 |
| 2004/0024513 A1 * | 2/2004 | Aizawa | B60T 8/4872 701/70 |
| 2008/0065293 A1 * | 3/2008 | Placke | B60K 31/0008 701/41 |
| 2013/0158838 A1 * | 6/2013 | Yorke | B60W 30/18018 701/103 |
| 2015/0012166 A1 * | 1/2015 | Hauler | B60W 30/0956 701/23 |
| 2016/0303972 A1 | 10/2016 | Kuhne | |
| 2016/0358475 A1 | 12/2016 | Prokhorov | |
| 2017/0045885 A1 * | 2/2017 | Okumura | B60W 30/00 |
| 2018/0119805 A1 * | 5/2018 | Cicala | F16H 3/66 |

FOREIGN PATENT DOCUMENTS

| | | | | |
|---|---|---|---|---|
| DE | 102009050404 A1 | | 5/2011 | |
| DE | 102011053780 A1 * | | 4/2012 | .......... F02N 11/0855 |
| DE | 102012200725 A1 | | 7/2013 | |
| DE | 102013019141 A1 | | 5/2015 | |
| DE | 102014000432 A1 | | 7/2015 | |
| DE | 102014015493 A1 | | 4/2016 | |
| DE | 102015118489 A1 | | 5/2016 | |
| DE | 102014225103 A1 | | 6/2016 | |
| DE | 102015109445 B3 | | 11/2016 | |
| EP | 2762988 A1 | | 8/2014 | |
| WO | WO-2011/026652 A2 | | 3/2011 | |

OTHER PUBLICATIONS

International Preliminary Report on Patentability directed to related International Patent Application No. PCT/EP2017/082218, dated Jun. 25, 2019, with attached English-language translation; 11 pages.

* cited by examiner

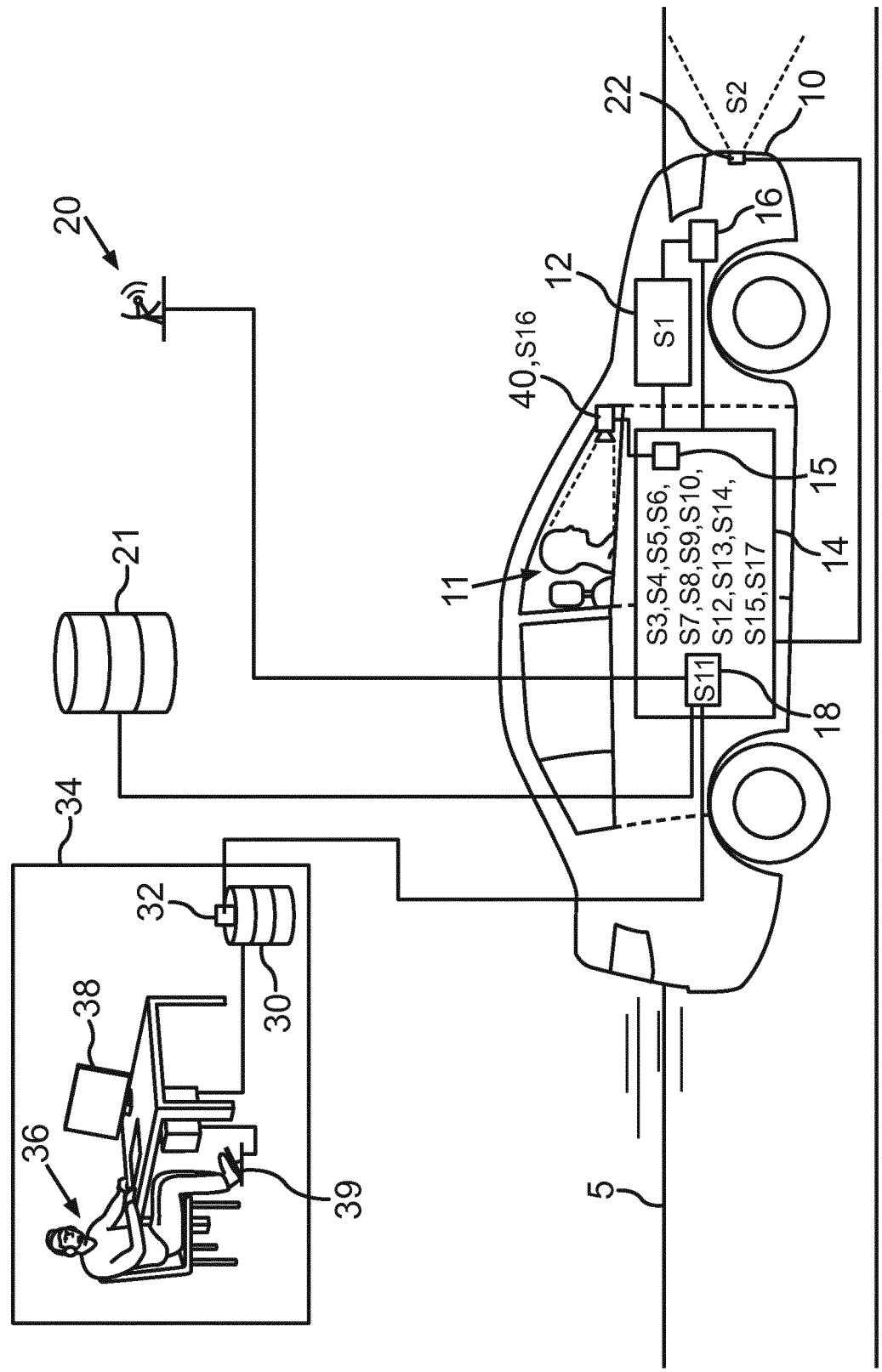

METHOD FOR OPERATING A DRIVER ASSISTANCE DEVICE OF A MOTOR VEHICLE

TECHNICAL FIELD

The disclosure relates to a method for operating a driver assistance device of a motor vehicle. A driver assistance device in this case is considered to be an electronic auxiliary device of the motor vehicle, which is configured to assist the driver in certain driving situations. The driver assistance device may, for example, include a driver assistance system, which is able to operate the motor vehicle in a fully autonomous or piloted driving mode. For this purpose, piloting data are provided, which described at least one operating parameter of a motor vehicle system of the motor vehicle or surroundings of the motor vehicle, and are navigation data. Based on the piloting data, the driver assistance device is able to ascertain all necessary settings for the piloted and/or fully autonomous driving mode.

BACKGROUND

Driver assistance systems assist the driver in certain driving situations, wherein a safety aspect is often a priority, but also an increase in driving comfort. Motor vehicle driving economy may also be improved. For this purpose, driver assistance systems may intervene in a drive and in a control as well as in signaling devices of the motor vehicle, and inform or warn the driver of the motor vehicle through a suitable user interface.

During piloted or fully autonomous driving by the driver assistance device, the latter requires the pieces of information of the piloting data, i.e., for example, an instantaneous speed of the motor vehicle, an acceleration, or a piece of information about a steering movement, wherein these exemplary pieces of information are referred to below as operating parameters of the motor vehicle system. The piloting data also include pieces of information about the surroundings of the motor vehicle or about characteristics of the surroundings such as, for example, pieces of information about a roadway marking, navigation data, pieces of information about a road course, guardrails or other road users. Driver assistance systems may also receive traffic signals from motor vehicle-external server devices, which may describe traffic congestion or a traffic flow, and are also referred to below as piloting data.

In hazardous situations, the control of the motor vehicle may be returned to the driver again, wherein the driver may be prepared by a corresponding warning sound or by a corresponding display on a screen. A driver assistance device is known from DE 10 2009 041 587 A1, with which the driver of a motor vehicle may easily recognize a hazardous situation during an autonomous parking process of the motor vehicle. The driver assistance device may receive instructions from a remote control and after receiving an interrupt instruction may interrupt a previously initiated parking process. Sensor signals of a camera may be transmitted to the remote control for monitoring the parking maneuver.

DE 10 2012 200 725 A1 describes a method for remotely controlling a vehicle, via which a user may communicate with the motor vehicle. The user is able with the aid of the remote control to transmit parameters for gas, brake and steering of the motor vehicle.

DE 10 2009 040 221 A1 describes the remote control of a motor vehicle, wherein a video camera of the motor vehicle may transmit a video image via a mobile radio connection.

DE 10 2014 015 493 A1 describes a method for operating a motor vehicle having at least one sensor device. Driver intervention data may be transmitted to the motor vehicle as a function of an operator control input of an operating person to a remote control device.

The cited prior art is directed either to the fact that the motor vehicle is controlled continuously via remote control or that a parking process is aborted by the user of the motor vehicle in a hazardous situation. However, the prior art does not touch upon the problem that an unplanned abort of the piloted or fully autonomous driving mode during a piloted or fully autonomous drive may occur or such an abort is imminent. Such is the case, for example, if a sensor malfunctions or if a sensor is no longer able to detect certain piloting data.

The prior art further presumes that the driver is alert and is able to immediately take control of the motor vehicle in the event of an unplanned abort of the piloted or fully autonomous driving mode. However, it may also be the case that the driver happens to be asleep or, in particular, is not immediately alert or able to concentrate if the motor vehicle has already driven a longer period of time in the piloted or fully autonomous driving mode.

Since a driver assistance system needs the piloting data, the corresponding sensor devices or other data sources must also function. A sensor device in this case is a unit or unit component, which is configured to detect the surroundings or a characteristic of the surroundings and includes at least one sensor. If, for example, an exterior camera for detecting a roadway marking is defective, then these data are not available to the motor vehicle. In another example, the motor vehicle may happen to be moving on a freshly tarred road on which the roadway marking is absent.

One object underlying the disclosure is to improve the take-over of the motor vehicle when the piloted or fully autonomous driving mode is aborted.

The object is achieved by the method according to the disclosure and by the devices according to the disclosure according to the independent patent claims. Additional advantageous refinements result from the sub-claims.

BRIEF DESCRIPTION OF THE DRAWINGS

FIG. 1 shows a schematic representation of the method for operating a driver assistance system of a motor vehicle, according to some embodiments of the disclosure.

DETAILED DESCRIPTION

The disclosure is based on the idea of employing a motor vehicle-external control center and/or a human vehicle pilot, who assumes control of the motor vehicle guidance when a piloted or fully autonomous driving mode is aborted. The motor vehicle-external control center—or the pilot, may communicate with the vehicle by means of a motor vehicle-external server device. Control of the motor vehicle may be taken over by a pilot or by the control center if the actual driver has fallen asleep, for example, and cannot be awakened quickly enough. Control may also already be surrendered if the motor vehicle is still driving autonomously or piloted but, for example, ends up in an unsafe situation due to conflicting pieces of sensor information.

The motor vehicle is initially operated by the driver assistance device in a piloted or fully autonomous driving mode, and piloting data is provided by the control device of the motor vehicle, which describes at least one operating parameter of a motor vehicle system of the motor vehicle and/or the surroundings of the motor vehicles, and/or are navigation data. A control device in this case is a unit or a unit component, which is configured for processing electronic data and for generating control signals and may be designed, for example, as a control board, a control chip or control unit. Exemplary piloting data were previously cited above.

The method according to the disclosure is characterized by the following steps implemented by the control device. Initially, it is checked whether a totality of the provided piloting data meets a piloting condition, the piloting condition stipulating a minimum requirement for the totality of the provided piloting data for implementing the piloted or fully autonomous driving mode. If the piloting condition is not met, i.e., upon failure to meet the piloting condition, an abort of the piloted or fully autonomous driving mode is determined. In the process, an abort that has already taken place or a probable abort at a future point in time may be determined. In other words, the abort may, for example, be predicted. A driving situation signal describing the provided piloting data is generated by the control device.

The driving situation signal is transmitted to a communication unit of a motor vehicle-external server device. This may take place, for example, by means of a communication unit of the motor vehicle. A communication unit in this case is understood to be a unit or a unit component, which is configured for hardwired or preferably wireless data transmission and for this purpose may include a transmitter and a receiver for an Internet or mobile radio connection according to a current mobile radio standard.

In a motor vehicle-external control center, in which the motor vehicle external server device may be housed, persons may be seated, for example, whose task it may be to take control of piloted or fully autonomous driving motor vehicles, or the motor vehicle-external server device may, for example, include a control unit or a control robot for automatically controlling the motor vehicle, wherein the control unit may then be referred to as a motor vehicle-external driver assistance device.

The control device receives at least one control signal from the motor vehicle-external server device for controlling the motor vehicle with the aid of the driver assistance device, preferably a control signal for operating the driver assistance device. The control device then transmits the control signal to the driver assistance device.

The control signal may advantageously be predefined and programmed, for example, by a human pilot, who is able to estimate and correspondingly react to an instantaneous driving situation of the motor vehicle with the aid of the piloting data. With the method according to the disclosure, control of the motor vehicle may be taken over by the exemplary human pilot if the driver has fallen asleep, for example, and cannot be awakened quickly enough. By surrendering control, a piloted driving may be continuously implemented for the user of the motor vehicle from his/her perspective, even if the motor vehicle is unable to implement this due, for example, to faulty sensor data and/or the driver is unable him/herself, for example, to take over control in a timely manner.

The checking of whether the totality of the provided piloting data meets the piloting condition, comprises a determination of a probability with which the piloted or fully autonomous driving mode may be implemented. If, in this case, the determined probability falls short of a predefined threshold value, it is predicted that the totality of the provided piloting data does not or will not meet the piloting condition. In other words, the control is transferred to a motor vehicle-external pilot in the event the motor vehicle in the interpretation of the piloting data "is unsafe", for example, if sensor data are conflicting and the driver assistance device implements the driving mode on the basis of the conflicting piloting data. A motor vehicle-external human pilot on the other hand may interpret the sensor signals using his/her human understanding and may intervene, which is why the driver assistance device is advantageously supported in unsafe or unclear situations.

According to one embodiment of the method according to the disclosure, a request signal describing a request for providing the control signal may be generated by the control device. In addition, a request signal may be transmitted to the communication unit of the motor vehicle-external server device. As a result, the exemplary human pilot is advantageously informed that the motor vehicle has implemented an abort of the piloted or fully autonomous driving mode or such an abort is probable.

The method according to the disclosure may also be adapted to situations, in which a piloted driving of motor vehicles is not allowed in principle, for example, on certain road sections or in certain zones. If these road sections or zones are characterized, for example, by navigation data as such zones or road sections, the control device may then determine that the motor vehicle is approaching a road section on which a piloted driving is not allowed and/or that the motor vehicle is situated on the road section. The checking may then reveal that the totality of the provided piloting data does not meet the piloting condition. In this case, the corresponding traffic signal or navigation signal describing the prohibition is considered to be a traffic signal or navigation signal describing piloting data.

Based the provided piloting data, the control device is able to ascertain a driving situation based on the provided piloting data, in which the motor vehicle is situated, and may then determine whether the totality of the piloting data meets a hazard criterion as a function of the determined driving situation. The hazardous situation criterion in this case is a criterion describing a hazardous situation, for example, fast driving on a freeway, in which it is important to take control of the motor vehicle as quickly as possible in the event of a possible abort of the driving mode. Not meeting the piloting condition is then a function of meeting the hazard criterion.

In other words, if, for example, the control device determines that the motor vehicle is driving at a very high speed on a freeway and that, for example, some sensor data are not conclusive, the hazardous situation criterion may then already be met. In another driving situation, for example, when parking on a large empty parking lot, the hazardous situation criterion is not met despite the inconclusive sensor data about the roadway marking.

The driving situation may, for example, be ascertained through navigation data, which may describe that the motor vehicle is located on the freeway or in the parking lot, and using, for example, a speed sensor, which is able to detect a high or a low speed.

Another exemplary hazardous situation criterion may be a lack of alertness on the part of the driver. If the control device detects a state of alertness of the user, for example, using sensor signals, which describe, for example, a line of vision or closed eyes and thus suggest a state of fatigue of the user, the control device may then determine based on the detected state of alertness whether the hazardous situation criterion is met. For example, a driver state signal generated by the control device may describe the detected state of alertness. The driving situation signal may then be generated as a function of meeting the hazardous situation criterion and/or of the driver state signal. As a result, the user may be bypassed as the weak link when taking control of the motor vehicle.

According to one refinement, an ascertainment of a latency period may be provided as a function of the detected state of alertness and/or of the driver state signal, which may be necessary for producing a prescribed degree of alertness of the user. The determination whether the hazardous situation criterion is met may be a function of the ascertained latency period. If, for example, the user is not looking exactly straight ahead but briefly through the side window, his/her alertness may be very quickly diverted back to the traffic events ahead of the motor vehicle by informing the user of the motor vehicle of the forthcoming take-over of the motor vehicle, for example, by a warning sound. If, for example, the user has closed his/her eyes and it may therefore be that the user is asleep, it may then take much longer to awaken the user and to restore him/her to a required state of alertness. In this case, surrendering to a pilot of the motor vehicle-external control center makes much more sense. The desired degree of alertness may be predefined, for example, by a value of a biometrical parameter, for example, a predefined minimum value of a pulse, wherein the biometric parameter may be continuously monitored, for example, by a corresponding sensor on, for example, a steering wheel or on an arm rest of the motor vehicle.

The piloting condition may preferably describe a predefined type, a predefined quality, or a predefined minimum number of available piloting data for implementing the piloted or fully autonomous driving mode. The predefined type or category may, for example, prescribe that camera data of an exterior camera are to be available in any case. A predetermined quality of the piloting data may mean, for example, that the various piloting data are complementary and not conflicting in their information. Finally, a minimum number of available pieces of piloting data may be predefined, which are to be necessary for implementation.

The above stated object is also achieved by a control device, which may preferably include a microcontroller and/or a microprocessor. The control device may, for example, be designed as a control unit or control board. The control device according to the disclosure is configured to implement the method steps relating to a control unit of one of the above described embodiments of the method according to the disclosure.

The above stated object is also achieved by a motor vehicle, for example, a passenger motor vehicle, including a driver assistance device, which is configured to implement a piloted and/or a fully autonomous driving mode. The motor vehicle is characterized by an embodiment of the control device according to the disclosure.

The disclosure also includes refinements of the method, which include features previously described in conjunction with the refinements of the motor vehicle according to some embodiments of the disclosure. For this reason, a description of the corresponding refinements of the method will not be repeated here.

Exemplary embodiments of the disclosure are described below.

FIG. 1 shows a schematic representation of the method for operating a driver assistance system of a motor vehicle, according to some embodiments of the disclosure.

The exemplary embodiments elucidated below are preferred embodiments of the disclosure. In the exemplary embodiments, the described components of the embodiments each represent individual features of the disclosure to be viewed independently of one another, which in each case refine the disclosure also independently of one another and, therefore, are to be considered as a component of the disclosure individually or in a combination other than the combination shown. Moreover, the described embodiment may also be supplemented by other of the previously described features of the disclosure.

Functionally identical elements in the FIGURE are each marked with the same reference numerals.

FIG. 1 shows by way of example the principle of the method according to some embodiments of the disclosure. For this purpose, a motor vehicle 10, designed for example, as a passenger motor vehicle, is located on a road section 5, for example, on a freeway section.

The motor vehicle 10 in this case includes a driver assistance device 12, which may include a driver assistance system known to a person skilled in the art. The driver assistance device 12 is configured to operate the motor vehicle 10 in a fully autonomous and/or piloted driving mode (method step S1). For this purpose, the driver assistance device 12 may be linked to one or to multiple motor vehicle systems 16, for example, to a braking system and/or to a steering system. Only one motor vehicle system 16 is shown in FIG. 1 for reasons of clarity. The link to the motor vehicle system 16 may be a direct data communication link (shown in FIG. 1 as a black connecting line), or else the data communication may flow via a control device 14 of the motor vehicle 10. The motor vehicle 10 in the example in FIG. 1 may, for example, be operated in a piloted driving mode (S1), and a user 11 of the motor vehicle 10 may happen to be tired or be sleeping.

The data communication links of the motor vehicle 10 may, for example, be data communication links of a data bus system of the motor vehicle 10. The control device 14 may preferably include a microcontroller or a microprocessor 15, and may, for example, be designed as a control unit or control board. To communicate with motor vehicle-external devices, the control device 14 may, for example, include a communication unit 18 which, for example, may include a transmitter for emitting mobile radio signals and/or a corresponding receiver.

To operate the motor vehicle 10 in the driving mode (S1), the driver assistance device 12 needs piloting data, which describe, for example, operating parameters of the motor vehicle 10 or of the motor vehicle system 16, and/or the surroundings of the motor vehicle 10, for example, the road section 5 or other road users, and/or navigation data, to name just a few examples of piloting data.

Navigation data may be received, for example from a satellite 20 or from a motor vehicle-external server device 21, wherein the exemplary server device 21 may, for example, be a server 21 of a traffic reporting service. The navigation data may, for example, describe pieces of cartographic information such as the coordinates where the motor vehicle 10 happens to be located, and/or map data. The server device 21 of the exemplary traffic reporting service may optionally transmit a traffic signal to the communication unit 18 of the control device 14, which may, for example, describe traffic congestion or slow-moving traffic on the road section 5, or a prohibition that states that motor vehicles 10 may not be piloted or operated fully autonomously on the road section 5.

Operating parameters, each of which describe an operating state of a motor vehicle system 16, may be received via the exemplary data bus system, wherein the operating parameter may describe, for example, a braking process, a steering movement or an acceleration of the motor vehicle 10. Corresponding motor vehicle systems 16 having suitable sensors are known to the person skilled in the art.

Pieces of information about the surroundings of the motor vehicle 10 and/or pieces of information about one respective characteristic of the surroundings may be detected, for example, via a sensor device 22 of the motor vehicle, which may include a camera or a radar on a front end or on other sides of the motor vehicle 10 and which are able to film the surroundings (S2). For reasons of clarity, only a small number of sensors is shown in FIG. 1. The piloting data may be transmitted directly to the driver assistance device 12, or initially to the control device 14, the piloting data being provided by the control device 14 (S3). In other words, the provision of the piloting data (S3) may, for example, be received by receiving corresponding signals directly from the exemplary sensor devices or from motor vehicle-external devices or, for example, may be retrieved by the driver assistance device 12.

The control device 14 checks whether the totality of the provided piloting data meets a piloting condition (S4). For example, it may be provided that it is cyclically checked whether the motor vehicle 10, i.e., the driver assistance device 12, is "roadworthy" again, i.e., is able to implement the piloted or fully automated driving mode (S1).

The piloting condition may, for example, be stored and predefined by a programming of the control device 14, so that at least pieces of information of each predefined type of piloting data must be available to enable the driver assistance device 12 to implement the piloted or fully autonomous driving mode (S1). The piloting condition may also prescribe that piloting data of certain motor vehicle systems 16, for example, data of the braking system and of a system for regulating a speed of the motor vehicle 10 must necessarily be available. In addition or alternatively, it may be provided, for example, that the different piloting data must be compared with one another and it must be ascertained whether these data are conflicting. The condition may then be that the pieces of information from the various sources of the piloting data must coincide, for example, up to at least 50% or up to at least 95%. If the exemplary navigation signal describes, for example, that the motor vehicle 10 happens to be located on a freeway, and the exemplary sensor device 22 transmits a camera image, for example, on which no roadway markings can be ascertained from an image analysis, these piloting data may then be conflicting.

As a result of the checking process S4, the control device 14 may ascertain, for example, whether the driving mode S1 is to be aborted due to conflicting piloting data, or a probability may be calculated, with which the piloted or fully autonomous driving mode S1 may be implemented (S5). For this purpose, the control device 14 may be configured with a corresponding programming. If, for example, it happens that the piloted or fully autonomous driving mode S1 may be reliably implemented with a probability of only 90%, it may be provided that the control device 14 compares this value with a threshold value stored in the control device 14. If, for example, a threshold value of 95% is stored, it may then be predicted that with this value falling short of the predefined threshold value, the totality of the provided piloting data does not meet the piloting condition (S6).

Alternatively or in addition, the piloting condition may be deemed not to be met if a traffic signal as described above advises that the road section 5 is not admissible, for example, for a piloted operation. By a comparison with the navigation data, the control device 14 may determine, for example, that the motor vehicle 10 happens to be located on or is approaching the road section (S7). For this purpose, the control device 14 may, for example, include a navigation software, which is able to compare the instantaneous position of the motor vehicle 10 with coordinates described to the traffic signal.

The failure to meet the piloting condition may have various causes. For example, piloting data may be lacking a sensor system may malfunction, only a second sensor system is able to deliver piloting data, or the driver assistance device 12 may reliably detect the driving situation and/or implement the piloted driving mode with a probability of, for example, only 50%.

Upon failure to meet the piloting condition, an abort of the piloted or fully autonomous driving mode is determined (S8), wherein the abort may be an abort implemented in fact, or a predicted or probable abort. At that point, a driving situation signal may be generated (S9), which describes the provided piloting data. The driving situation signal may optionally also describe the determined abort or a predicted abort. The control device 14 may also generate a request signal (S10), which may describe a request for providing a control signal.

In the method step S11, the driving situation signal is transmitted to a communication unit 32 of a motor vehicle-external server device 30. Optionally, the request signal may also be transmitted in the method step S11 to the communication unit 32 of the server device 30. This server device 30 may include, for example, a server which may be situated in a motor vehicle-external control center 34, wherein a pilot 36 or a control computer may be in the control center 34 for taking over the control operation of the motor vehicle 10. The request signal may be output in the control center 34, for example, by a screen 38 or as a warning sound through a loudspeaker.

The driving situation signal may also be output in the control center 34, wherein a camera image of the sensor device 22 is displayed on the screen 38, for example. The additional piloting data, for example, may also be displayed on the screen 38. In the example in FIG. 1, the human pilot 36 takes over control of the motor vehicle 10 and has a corresponding control technology at his/her disposal, which may have, for example, among other things, a brake and/or accelerator pedal 39, a handle, or a joystick (not shown in FIG. 1) for steering the motor vehicle 10. Alternatively, control commands may be predefined by a keypad input and a corresponding control signal for operating the driver assistance device 12 may be generated by the server device 30. The control device 14 of the motor vehicle 10 receives the control signal in the method step S12 from the server device 30 and is able to forward (S13) this to the driver assistance device 12.

Once the human pilot 36 has taken over control of the motor vehicle 10 or of the operation of the driver assistance device 12, the user 11 of the motor vehicle 10 may then continue to sleep or, for example, may be awakened by the motor vehicle 10. Because an awakening may take longer, for example, such a latency period is bridged by the human pilot 36 and/or by the server device 30.

An instantaneous driving situation may be ascertained (S14) based on the provided piloting data. In the method step S15, it may then be ascertained whether the totality of the provided piloting data meets a hazardous situation criterion as a function of the ascertained driving situation, which may be the case in the example of FIG. 1, if during rapid driving on the freeway, for example, the sensor device 22 malfunctions or recommends an absent roadway marking. In contrast to a situation, for example, in which the motor vehicle 10 happens to park in an available parking space in a piloted driving mode, the malfunction of the sensor device 22 or the lack of roadway marking may represent a safety risk, and the piloting condition cannot be met as a result. In other words, the piloting condition may be a function of the ascertained driving situation.

The hazardous situation criterion may also be met if, for example, it is determined that the driver 11 is not very alert. For this purpose, a sensor device 40 may include a camera for detecting a line of vision, and/or a sensor for monitoring biometric parameters such as detecting a deep sleep (S16). Such a sensor device 40 may detect corresponding parameters (S16), for example, a line of vision, a pulse or a degree of eyelid closure of the user 11. From this data, which described the state of alertness of the user 11, the control device 14 may determine whether the hazardous situation criterion is met (S15).

In this way, the sensor device 40, for example, may detect a driving behavior of the user 11 (S16). Additional examples are a detection of a head movement, a detection of a line of vision, a detection of a viewing direction, or a detection of a telephone call of the user 11, which is why he/she is perhaps not able to be very alert in the moment. Such a telephone call may be identified, for example via a Bluetooth interface. Comparison data may be stored, for example in the control device 14, which may assign a respective value of a frequency of head movement to the predefined degree of alertness of the user 11. Similarly, a corresponding comparison data set may be stored for evaluating the line of vision and the viewing direction.

A latency period may be ascertained as a function of the detected state of alertness (S17), which is necessary for establishing a predefined degree of alertness of the user 11. This latency period is very minimal, for example, in the case of a telephone call, since the user 11 may respond immediately to a warning sound. The latency period may be very long, however, if the user 11 is in a deep sleep. Corresponding comparison data may be stored in the control device 14.

The above described exemplary embodiment illustrates the principle of the method according to the disclosure to surrender the piloted and/or fully autonomously driving motor vehicle 10, for example, to a human pilot 36 when the piloted or fully autonomous driving is aborted, for example, due to faulty sensor data.

According to another exemplary embodiment, this human pilot 36 may, for example, be located in a control center 34. A camera image and all surroundings sensor data may be transmitted to the pilot 36 (S11) and the pilot is able to control the vehicle motor vehicle 10 over distance by means of data transmission.

According to another exemplary embodiment, it may be provided that such a control may already be surrendered if the motor vehicle 10 is still driving piloted or autonomously, but it may end up in an unsafe situation due to conflicting pieces of sensor information.

According to another exemplary embodiment, it may be provided that upon failure to meet the piloting condition, the piloted or fully autonomous driving mode (S1) may be actively aborted by means of a corresponding abort signal of the control unit 14, which may be transmitted to the driver assistance device 12, during or before or after control is surrendered to the server device 30 and/or to the human pilot 36.

The invention claimed is:

1. A method for operating a driver assistance device of a motor vehicle, comprising:
   operating, by the driver assistance device, the motor vehicle in a piloted or fully autonomous driving mode;
   providing, by a control device of the motor vehicle, piloting data which describe at least one operating parameter of a motor vehicle system of the motor vehicle or surroundings of the motor vehicle, or are navigation data;
   checking, by the control device, whether a totality of the provided piloting data meets a piloting condition, wherein the piloting condition stipulates a minimum requirement for the totality of the provided piloting data for implementing the piloted or fully autonomous driving mode, and wherein the checking whether the totality of the provided piloting data meets the piloting condition comprises:
      determining a probability with which the piloted or fully autonomous driving mode may be implemented; and
      predicting that the totality of the provided piloting data does not meet the piloting condition based on the determined probability falling short of a predefined threshold value;
   determining, by the control device, whether the totality of the provided piloting data meets a hazardous situation criterion, comprising:
      detecting a state of alertness of a user of the motor vehicle;
      ascertaining a latency period as a function of the detected state of alertness; and
      determining whether the hazardous situation criterion is met based on the ascertained latency period;
   determining, upon failure to meet the piloting condition or upon meeting the hazardous situation criterion, an abort of the piloted or fully autonomous driving mode and generating a driving situation signal, the driving situation signal describing the piloting data;
   transmitting, by the control device, the driving situation signal to a communication unit of a server device, the server device being external to the motor vehicle;
   receiving, by the control device, at least one control signal from the server device for operating the driver assistance device; and
   transmitting, by the control device, the control signal to the driver assistance device.

2. The method of claim 1, further comprising:
   generating, by the control device, a request signal which describes a request for providing the control signal; and
   transmitting, by the control device, the request signal to the communication unit of the server device.

3. The method of claim 1, further comprising:
   determining, by the control device, that the motor vehicle is approaching a road section on which the piloted or fully autonomous driving mode is not allowed, or that the motor vehicle is located on the road section, wherein the checking indicates that the totality of the provided piloting data fails to meet the piloting condition.

4. The method of claim 1, further comprising:
   ascertaining, by the control device, a driving situation based on the provided piloting data, in which the motor vehicle is situated; and determining, by the control device, whether the totality of the provided piloting data meets the hazardous situation criterion as a function of the ascertained driving situation, wherein the failure to meet the piloting condition is a function of meeting the hazardous situation criterion.

5. The method of claim 1, further comprising:
determining, via the control device, whether the hazardous situation criterion is met based on the detected state of alertness.

6. The method of claim 1, further comprising:
establishing a predefined degree of alertness of the user based on the ascertained latency period.

7. The method of claim 1, wherein meeting the piloting condition comprises:
meeting a predefined type, a predefined quality, or a predefined minimum number of the available piloting data for implementing the piloted or fully autonomous driving mode.

8. A motor vehicle, comprising:
a driver assistance device configured to operate the motor vehicle in a piloted or fully autonomous driving mode;
a sensor device configured to detect a state of alertness of a user of the motor vehicle; and
a control device, wherein the control device comprises a microcontroller or a microprocessor, and is configured to:
provide piloting data which describe at least one operating parameter of a motor vehicle system of the motor vehicle or surroundings of the motor vehicle, or are navigation data;
check whether a totality of the provided piloting data meets a piloting condition, wherein the piloting condition stipulates a minimum requirement for the totality of the provided piloting data for implementing the piloted or fully autonomous driving mode, and wherein to check whether the totality of the provided piloting data meets the piloting condition, the control device is configured to:
determine a probability with which the piloted or fully autonomous driving mode may be implemented; and
predict that the totality of the provided piloting data does not meet the piloting condition based on the determined probability falling short of a predefined threshold value;
determine whether the totality of the provided piloting data meets a hazardous situation criterion, comprising:
ascertain a latency period as a function of the detected state of alertness; and
determine whether the hazardous situation criterion is met based on the ascertained latency period;
determine, upon failure to meet the piloting condition or upon meeting the hazardous situation criterion, an abort of the piloted or fully autonomous driving mode and generate a driving situation signal, the driving situation signal describing the piloting data;
transmit the driving situation signal to a communication unit of a server device, wherein the server device is external to the motor vehicle;
receive at least one control signal from the server device for operating the driver assistance device; and
transmit the control signal to the driver assistance device.

9. The motor vehicle of claim 8, wherein the sensor device comprises
a camera or a biometric sensor.

10. The motor vehicle of claim 8, wherein the control device is further configured to:
generate a request signal which describes a request for providing the control signal; and
transmit the request signal to the communication unit of the server device.

11. The motor vehicle of claim 8, wherein the control device is further configured to:
determine that the motor vehicle is approaching a road section on which the piloted or fully autonomous driving mode is not allowed, or that the motor vehicle is located on the road section, wherein the checking indicates that the totality of the provided piloting data fails to meet the piloting condition.

12. The motor vehicle of claim 8, wherein the control device is further configured to:
ascertain a driving situation based on the provided piloting data, in which the motor vehicle is situated; and
determine whether the totality of the provided piloting data meets the hazardous situation criterion as a function of the ascertained driving situation, wherein the failure to meet the piloting condition is a function of meeting the hazardous situation criterion.

13. The motor vehicle of claim 8, wherein the control device is further configured to:
determine whether the hazardous situation criterion is met based on the detected state of alertness.

14. The motor vehicle of claim 8, wherein the control device is further configured to:
establish a predefined degree of alertness of the user based on the ascertained latency period.

15. The motor vehicle of claim 8, wherein the piloting condition describes:
a predefined type, a predefined quality, or a predefined minimum number of the available piloting data for implementing the piloted or fully autonomous driving mode.

* * * * *